United States Patent [19]

Kötzsch et al.

[11] Patent Number: 4,824,979
[45] Date of Patent: Apr. 25, 1989

[54] METHOD FOR THE PREPARATION OF PARTIAL ESTERS AND ORTHO ESTERS OF TITANIUM, ZIRCONIUM OR HAFNIUM

[75] Inventors: Hans-Joachim Kötzsch, Rheinfelden; Hans-Günther Srebny, Stolzenau; Hans-Joachim Vahlensieck, Wehr, all of Fed. Rep. of Germany

[73] Assignee: Huels Troisdorf AG, Cologne, Fed. Rep. of Germany

[21] Appl. No.: 810,514

[22] Filed: Dec. 18, 1985

[30] Foreign Application Priority Data

Dec. 24, 1984 [DE] Fed. Rep. of Germany ....... 3447297

[51] Int. Cl.$^4$ .............................. C07F 7/28; C07F 7/00
[52] U.S. Cl. ........................................... 556/54; 556/56
[58] Field of Search ..................... 556/54, 56

[56] References Cited

U.S. PATENT DOCUMENTS

| | | | |
|---|---|---|---|
| 2,187,821 | 1/1940 | Nelles | 556/54 |
| 2,512,058 | 6/1950 | Gulledge | 556/54 X |
| 2,654,770 | 10/1953 | Herman | 556/54 |
| 2,663,720 | 12/1953 | Hill | 556/54 |
| 2,727,918 | 12/1955 | Boyd | 556/56 X |
| 3,056,818 | 10/1962 | Werber | 556/56 X |
| 3,277,131 | 10/1966 | Schön et al. | 556/56 X |
| 3,547,966 | 12/1970 | Marble | 556/54 X |
| 3,641,079 | 2/1972 | Termin et al. | 556/56 X |
| 3,754,011 | 8/1973 | Hoch | 556/54 X |

OTHER PUBLICATIONS

Feld et al., *The Organic Chemistry of Titanium*, Butterworths Inc., Washington, D. C., ©1965, pp. 46–57.
Chemical Abstracts vol. 67: 44276g (1967).
Chemical Abstrats vol. 97: 72486p (1982).
Chemical Abstracts vol. 99: 158922f (1983).
Nesmeyanov et al., Doklady Akad. Nauk S.S.S.R. 94 (1954), pp. 249–252 (with abstract).
Chemical Abstracts, Jul. 20, 1970, vol. 73, No. 3, p. 373, Abstract 14906u "Reaction of Trimethylmethoxysilane With Titanium Tetrachloride".
Chemical Review, vol. 61, pp. 1 to 15, "The Organic Chemistry of Titanium", Isao Shihara et al., May 3, 1960.

*Primary Examiner*—Patrick P. Garvin
*Assistant Examiner*—George R. Fourson
*Attorney, Agent, or Firm*—Felfe & Lynch

[57] ABSTRACT

Disclosed is a new method for the preparation of metallic acid esters of titanium, zirconium or hafnium wherein a halide of the metal reacts with an organosilane ester, resulting in the formation of partial esters of the metallic acids. The degree of esterification of the metallic acid ester can be controlled based on the organosilane ester and it is possible to obtain complete esterification of the metal halides. The metallic acid partial esters prepared by the method are very pure, and can be separated selectively from the mixture in a simple manner. The metallic acid alkyl esters obtained can very easily be further esterified to the metallic acid tetraalkyl esters with the formation of very pure tetraalkyl esters.

12 Claims, No Drawings

METHOD FOR THE PREPARATION OF PARTIAL ESTERS AND ORTHO ESTERS OF TITANIUM, ZIRCONIUM OR HAFNIUM

BACKGROUND OF THE INVENTION

The subject matter of the present invention is a method for the preparation of partial esters and ortho esters of titanium, zirconium or hafnium by esterifying the corresponding metal halides. The term, "partial esters of titanium, zirconium or hafnium," which are also referred to herein as metal acid partial esters or halogen partial esters, is to be understood to refer to compounds of the formula $(RO)_n MeX_{4-n}$, in which R can represent alkyl moieties of 1 to 18 carbon atoms, preferably 2 to 8 carbon atoms, or aryl moieties, X represents halogen, preferably chlorine, and n can assume values between 1 and 3.

It is known to prepare ortho esters, especially of titanium and zirconium, on a large technical scale exclusively by reacting the corresponding tetrachlorides with desired organic hydroxy compounds in the presence of amines as acid acceptors and solvents as diluents (cf. J. Nelles, U.S. Pat. No. 2,187,821; CA 34 3764).

A significant drawback of this process is the large amount of amine hydrochlorides produced as waste. The titanium and zirconium ortho esters made in this manner contain considerable amounts of polymers in addition to the usually present solvent and alcohol or phenol moieties. The polymers result from the secondary reaction occurring mainly in the first two stages of esterification with alcohols and resulting in the formation of alkyl halide which simultaneously forms water and which hydrolyzes the metal esters with the simultaneous formation of quality-degrading metal oxane.

Direct esterification, i.e., the reaction of the titanium or zirconium tetrahalides with organic hydroxy compounds with the release of gaseous hydrogen halide, is known to be very slow. Orthoesters, in the absence of amines, can be obtained in this manner only from phenols used in massive excess. The excess phenol, however, is stubbornly retained by the product, so that these products cannot be used as pure ortho esters. On the other hand, direct esterification using aliphatic alcohols does not lead to the ortho ester, but runs slowly as far as the dihalogen diester ("half ester"), and then stops, even with an alcohol excess. The monohalotriesters, which are sought after on account of their stereoselective catalyst properties, are not accessible at all by direct esterification. The very special disadvantage of this known process is also, in the case of aliphatic esters, the pronounced tendency towards the secondary reaction of alkyl halide and water formation and the formation of polymers.

The partial esters of titanium and zirconium, especially the half esters and the triester monohalides, are of considerable interest especially on account of their outstanding catalytic properties in the production of tactic polymers on Ziegler-Natta catalysts, and in stereoselective syntheses in organic chemistry. The attempt has therefore already been made to prepare these partial esters by mixing the ortho esters with the tetrahalides in a controlled equivalent ratio with the intention of obtaining the desired partial ester structure in the partial ester mixture that forms in this process, and which of course contains all stages of esterification in addition to the foreign substances and polymers brought in from the ortho esters, obtaining them at least in an appreciable percentage if not in pure form. For lack of purer products, such partial ester mixtures are presently used as catalyst components with somewhat useful results. However, what is involved is not pure partial esters having a clearly assured structure.

The state of the art thus described is unsatisfactory insofar as, if pure partial esters can be used in the above-described applications, a decided advance could be expected with regard to stereoselectivity or even stereospecificity and tacticity.

Accordingly, the problem was to find an effective method for a highly selective production of pure halogen partial esters and ortho esters of titanium and zirconium, in which the production of ammonium halide will be considerably reduced or completely eliminated.

THE INVENTION

As the solution of this problem a method has been found for the preparation of metallic acid esters of the formula $(RO)_n MeX_{4-n}$, in which Me represents a metal of the group, titanium, zirconium and hafnium, R represents identical or different saturated or unsaturated aliphatic or aromatic hydrocarbon moieties, and X represents halogen, and n can assume values from 1 to 4. The corresponding metal halide is selectively reacted with the equivalent amounts of organosilane esters necessary for the desired degree of esterification, and then, if desired, for the preparation of metallic acid alkyl esters in which n can assume values of 3 to 4, bringing the metallic acid partial esters, with $n=1$ to 3, into reaction, in a known manner, with an organic hydroxy compound in the presence of an amine. When this procedure is applied, the desired partial esters are selectively obtained in a heretofore never achieved high purity.

Another important advantage of the process according to the invention is its faster and immediate reaction, and especially the approximately quantitative yield of product in every single case, with the complete absence of secondary reactions, even though compounds of the type $Ti(OSiR'_3)_4$ are known as being remarkably stable (cf. Encyclopedia of Chemical Technology, vol. 20, 2nd ed., p. 452) and their formation by transesterification would be expected based on present knowledge.

In comparison with the conventional method for the preparation of ortho esters with the use of acid acceptors, the method according to the invention offers the extraordinarily important advantage that the forced production of ammonium salts is prevented in the most favorable case, but at a minimum is reduced by one-half.

The process according to the invention corresponds basically to the following equation (1):

$$-MeX_p + (RO)_{4-n}-SiR'_n \longrightarrow -MeOR + X_p(OR)_{4-n-p}SiR'_n$$

in which Me, X and R have the meaning given above, R' represents alkyl groups of 1 to 4 carbon atoms, n can assume values of 1 to 3 and p values of 1 to 3, on the condition that, in the formula for the alkyl-alkoxy-halogen silanes, $2 \leq n+p \leq 4$. Accordingly, when mono- or dialkylalkoxy silanes are used, first the chloralkoxymono- or dialkylsilane forms, before an additional alkoxy group of the silane reacts with an additional halogen atom of the metal compound.

Each of the three partial ester stages can, of course, also be further esterified in a known manner, for example with amines and organic hydroxy compounds (ROH), with the splitting off of amine hydrohalides. Often a complete isolation of the particular partial ester stage is not necessary, especially when this partial ester is used for further reaction with alcauols and amines to obtain the ortho-esters with m=4. An isolation is preferred when the partial ester shall be the desired end-product. The isolation of the metallic acid partial and ortho esters prepared according to the invention, and of the silane halides forming in this process, is performed according to the physical properties of these products by conventional methods which are used, for example, in distillation, vacuum distillation, solid extraction, or crystallization.

Starting substances for the process according to the invention are, on the one hand, the tetrachlorides, tetrabromides and tetraiodides of titanium, zirconium and hafnium, the chlorides being used preferentially, and on the other hand organosilane esters of the following formula I:

$$R'_nSi(OR)_{4-n}(n=1, 2 \text{ or } 3) \quad (I)$$

in which R represents saturated or unsaturated aliphatic moieties which can be branched and/or cyclic and/or aromatically substituted and/or contain ether oxygen bridges, or aromatic moieties which can have hydrocarbon and/or halogen and/or nitro substituents. R' represents identical or different alkyl groups of 1 to 4 carbon atoms.

Suitable trialkyl silyl esters which come under general formula I are, for example, the trimethyl, triethyl, ethyldimethyl, propyldimethyl, n-butyldimethyl, isobutyldimethyl, tertiarybutyldimethyl and tripropylsilyl esters of methanol, ethanol, n- and isopropanol, allyl alcohol, n-, iso-, secondary and tertiary butanol, cyclopentanol, cyclohexanol, 2-ethylhexanol, the octanols, the nonanols, decanol, dodecyl alcohol, cetyl alcohol, octadecyl alcohol, oleanol, isoborneol, menthol, ethylene glycol monomethyl ether, triethylene glycol monomethyl ether, 2-methoxypropanol, 1-methoxypropanol-(2), benzyl alcohol, benzhydrol, phenol, o-, m- and p-cresol, the xylenols, o-, m- and p-chloro-, -bromo- and -iodophenol, 4-chloro-3,5-xylenol, 2,4,6-trichloro-3,5-xylenol, pentachlorophenol, nonylphenol, alpha- and beta-phenol, 9-anthranol, etc. The aromatic hydroxy compounds accordingly have methyl or ethyl groups as the preferred alkyl substituents.

Dialkyl silyl diesters of general formula I suitable for the practice of the method of the invention are, for example, the dimethyl, ethylmethyl, propylmethyl, n-butylmethyl, isobutylmethyl, diethyl and dipropyl silyl diesters of the listed organic hydroxy compounds.

Alkyl silane triesters of general formula I which are suitable for the practice of the method of the invention are, for example, the methyl, ethyl, n-propyl, isopropyl, n-butyl, isobutyl and tertiary butyl silyl triesters of the listed organic hydroxy compounds.

The named alkyl silyl esters can easily be prepared in a known manner, for example by reacting alkyl chlorosilanes or alkyl silyl amines with organic hydroxy compounds.

The process according to the invention can be performed, if desired, in inert solvents. Suitable inert solvents are, of course, the alkyl alkoxy halogen silanes that form in the reaction according to the invention. However, aliphatic, aromatic and/or chlorinated hydrocarbons and/or ethers are also suitable. In detail, they are, for example, the pentanes, hexanes, heptanes, isooctane, cyclohexane, methyl cyclohexane, decalin, benzine fractions such as petroleum ether or ligroin, tetralin, benzene, toluene, the xylenes, aromatic benzines such as Shell Sol H, methylene chloride, chloroform, carbon tetrachloride, trans-dichloroethylene, trichloroethylene, perchloroethylene, chlorbenzene, the dichlorbenzenes, 1,1,1-trichloroethane, trichlorotrifluoroethane, 1,1,1,3-tetrachloropropane, diisopropyl ether, tetrahydrofuran, ethylene glycol diethyl ether, etc.

In practice, the process of the invention is performed in a normal stirrer reactor with reflux condenser, under anhydrous conditions, of course. As a rule, the titanium, zirconium or hafnium halide is placed in the reactor together with a suitable solvent or suspension medium and brought to the reaction temperature, and finally the alkyl silane ester is dosed in, in the amount of one, two, three or four equivalents, depending on the desired degree of esterification.

The process of the invention is performed preferably at standard pressure, but the application of an elevated pressure may be advantageous in certain cases. On the other hand, vacuum is applied if the boiling temperatures are to be lowered.

The choice of the reaction temperature depends on the desired degree of esterification. The monoesters and diesters form very easily and rapidly at room temperature. However, to avoid any delays in starting, it is advantageous to operate with a slightly elevated temperature, at least at the beginning. The temperature range preferred for this purpose is between 40° C. and 120° C. When operating without solvent it is desirable to select as the working temperature the boiling temperature of the alkyl halogen silane that is forming, if it is within the temperature range described above as preferred.

The triesters and ortho esters are prepared preferably at higher temperatures, namely in the range between 40° C. and 230° C. It can be advantageous to distill the developing halogen alkyl silane out during the reaction. The stirrer reactor is equipped for this purpose with a column in order to suppress the simultaneous distillation of unreacted silane ester.

The immediate distillation of the halogen silane that forms in the reaction, however, is not necessary in all cases. Solid metallic acid partial esters can, in accordance with the invention, also be harvested by crystallizing them out of the completely reacted reaction solution and isolated by conventional, ordinary methods for the separation of solids.

Another embodiment of the process according to the invention consists in placing in the reactor the equivalent amount of alkyl silane ester necessary for the desired degree of esterification, preferably at its boiling temperature, and then dosing in the titanium, zirconium or hafnium tetrachloride, dissolved (preferably, in the case of the latter two metal chlorides) in a suitable inert solvent.

One special embodiment of the process according to the invention is the esterification of the titanium, zirconium or hafnium chlorides with esters of the general formula I produced in situ. This procedure is performed preferably at standard pressure, namely, the metal halide is placed in the reactor together with an excess of 0.1 to 6 equivalents of a trialkyl chlorosilane. The mixture of starting materials is heated to ebullition. Then the ester component in the form of the organic hydroxyl compound (ROH) is gradually introduced with constant stirring, for example through a capillary tube submerged in the boiling liquid phase of the reaction mixture, at a rate corresponding to the progress of the reaction, and in the equivalent amount corresponding to the desired degree of esterification. This causes the release of hydrogen chloride which is removed for reuse through the reflux condenser and a gas condenser operating at low temperature. When the addition of the ester component is completed, the mixture is refluxed until all of the hydrogen chloride has been driven off (this is generally the case after about 30 minutes) and lastly it is worked up, for example by distilling out the trialkylchlorosilane etc., or, if solid reaction products are involved, by crystallization, etc.

The reaction according to the invention does not lead to the fourth esterification stage with all of the above-named organosilane esters, i.e., to the production of the corresponding metallic acid ortho esters. Especially the organosilane alkyl esters permit the production of metallic acid partial esters only up to the third stage of esterification. Even when more than three mole-equivalents of organosilane alkyl esters are used per mole of metal halide, metallic acid partial esters are obtained with no more than three alkoxy groups per metal atom. On the other hand, organosilane aryl esters react with the metal halides up to the fourth stage of esterification. By the procedure in accordance with the invention it is accordingly possible to produce the desired metallic acid ortho aryl esters in a simple manner, in very pure form.

In accordance with the invention, the ortho alkyl esters of the named metallic acids can be prepared by producing a metallic acid partial alkyl ester by the reaction, in accordance with the invention, of metal halide with organosilane alkyl esters, and, after separating the alkyl halogen silane by distillation, performing the reaction to the ortho ester in a manner known in itself. Without further isolation of the partial ester, the reaction mixture then resulting is made to react with an amine in a stoichiometric rate depending on the used alcohol serving as an acid acceptor, and with the remaining stoichiometric amount of the alkyl alcohol that is still needed, with respect to the remaining halogen content. At the same time, the remaining halide content of the partial ester is bound in the form of amine hydrohalide with the formation of the ortho ester. This reaction is virtually quantitative and virtually free of secondary reactions.

Subject matter of the present invention is accordingly also the use of the metallic acid partial esters prepared by the claimed process, and especially of the metallic acid partial alkyl esters, for the preparation of monohalogen triesters, and especially for the preparation of the metallic acid tetraalkyl and aryl esters. In general, complete isolation of the partial esters is not necessary. However, the use of completely isolated partial esters is possible for the preparation of especially pure tetraalkyl esters.

In comparison with the known procedure of using the tetrahalides as starting components, the reduced production of waste salts in the invention constitutes a considerable advantage. A salient and most important advantage of the method of the invention and of the use of the partial esters in the preparation of the ortho esters, however, is the absence of the formation of alkyl chloride and water by an undesirable secondary reaction, especially when the monohalogen triester and the dihalogen diester are used as starting components, so that the ortho esters prepared in this manner are formed with higher yields and are substantially purer, e.g., free of polymers, than the corresponding ortho esters made by known methods.

The metallic acid esters prepared by the method of the invention, particularly the partial esters, and the ortho esters prepared without the addition of amine, or with the aid of smaller amounts of amine than in conventional methods, satisfy very high quality requirements as regards their purity or their content of active substance. They are worked up, as a rule, by simply evaporating the halogen organosilane that has formed, and the solvent used, if any, in vacuo, if desired. In the case of the ortho esters in whose preparation the known amine process was used in part, the ammonium salt may still have to be separated. The metallic acid partial esters and ortho esters obtained in this manner can be used for all known applications on account of their satisfactory purity. The conventional methods of distillation, especially those of vacuum distillation, can be used as additional methods for working up the product. For products in a solid state of aggregation under normal conditions, the common methods of solid separation by crystallization, for example in a crystallizer, phase separation, for example by sedimentation or filtration, and drying, can be used.

The products prepared by the method of the invention are, on the one hand, the trialkyl halogen silanes which can be reused if desired, such as, for example, trimethylchlorosilane, trimethylbromosilane, trimethyliodosilane, triethylchlorosilane, ethyl dimethylchlorosilane, propyl dimethylchlorosilane, n-butyl-dimethylchlorosilane, isobutyldimethylchlorosilane, tert.butyldimethylchlorosilane, tripropylchlorosilane, etc., or the dialkyl dihalogen or dialkylhalogenalkoxy silane such as dimethylchlorosilane, dimethylmethoxychlorosilane, dimethylethoxychlorosilane, methylethyldichlorosilane, methylethylmethoxychlorosilane, methylethylethoxychlorosilane, methylisobutyldichlorosilane or the alkyl trihalogen or dihalogenalkoxy or alkyl halogendialkoxysilanes, such as, for example, methyltrichlorosilane, methylmethoxydichlorosilane, methyldimethoxychlorosilane, ethyltrichlorosilane, ethylethoxydichlorosilane, ethyldiethoxychlorosilane, isobutyltrichlorosilane etc., and on the other hand the desired metal esters. The last include monoester trihalides, diester halides, triester monohalides, and ortho esters.

The following are given as examples: methoxytitanium trichloride, methoxyzirconium trichloride, ethoxytitanium trichloride, ethoxyzirconium trichloride, n-propoxytitanium chloride, n-propoxyhafnium trichloride, isopropoxytitanium trichloride, isopropoxyzirconium chloride, allyloxytitanium trichloride, the butoxytitanium (or zirconium, or hafnium) trichlorides, cyclohexyloxytitanium trichloride, 2-ethylhexoxytitanium trichloride, 2-ethylhexoxyzirconium trichloride, omega-methoxytriethyleneglycoloxytitanium trichloride, 2-methoxyisopropoxytitanium trichloride, phenoxytitanium trichloride, phenoxyzirconium trichloride, p-bromophenoxytitanium chloride, p-iodophenoxytitanium trichloride, etc.

Examples of diester halides are the following: diethoxytitanium (or zirconium) dichloride, diethoxytitanium (or zirconium) dibromide, diethoxytitanium diiodide, di-n-propoxy-titanium dichloride, di-n-propoxyzirconium (or hafnium) dichloride, diisopropoxytitanium dichloride, diisopropoxyzirconium dichloride, diallyloxytitanium dichloride, the di-butoxytitanium (or zirconium or hafnium) dichlorides, dicetyloxytitanium dichloride, di-2-methoxyisopropoxytitanium dichloride, di-2-methoxyisopropoxyzirconium dichloride, dibenzyloxytitanium dichloride, dibenzohydryloxytitanium dichloride, dibenzohydryloxyzirconium dichloride, diisobornyloxytitanium dichloride, diisobornyloxyzirconium dichloride, diphenoxytitaniumdichloride, di-p-cresyloxy-titanium dichloride, di-(4-chloro-3,5-xylenoxy) titanium dichloride, di-alpha-naphthoxytitanium dichloride, di-alpha-naphthoxyzirconium dichloride, di-p-nonylphenoxytitanium dichloride, di-9-anthranoloxytitanium dichloride.

Furthermore, the corresponding triester monohalides as well as the following ortho esters, for example, can be prepared: tetramethoxytitanium, tetraethoxytitanium, tetraethoxyzirconium, tetra-n-propoxytitanium, tetra-n-propoxyzirconium tetra-n-propoxyhafnium, tetraallyltitanate, tetraallylzirconate, the tetrabutoxy (or zirconium or hafnium) compounds, tetra-2-ethylhexyltitanate, tetra-2-ethylhexylzirconate, tetracyclohexyltitanate, tetracyclohexylzirconate, tetraacetylzirconate, tetraisobornyltitanate, tetraisobornylzirconate, tetrastearyltitanate, tetrastearylzirconate, tetra-2-methoxyisopropoxytitanium, tetra-2-methoxyisopropoxyzirconium, tetrakis-omega-methoxytetraethyleneglycoloxytitanium, tetrakis-omega-methoxytetraethyleneglycoloxyzirconium, tetrabenzyltitanate, tetrabenzylzirconate, tetrabenzohydryltitanate, tetrabenzohydrylzirconate, tetracresyltitanate, tetracresylzirconate, tetraxylenyltitanate, tetraxylenylzirconate, tetrakisnonylphenoxytitanium, tetrakisnonylphenoxyzirconium, and tetra-4-choloro-3,5-xylenoxytitanium.

These products, prepared by the method according to the invention in virtually quantitative yields throughout, are of a high purity previously never achieved. This quality is to be seen especially in their spectral data and in other analyses. Therefore it is not surprising that the products made by the method of the invention differ in their physical characteristics, especially their melting points, colors, densities and viscosities from the data previously obtained on presumably the same substances or on such substances in impure form of the same name, and evidently in need of correction, and in most cases they have substantially different properties than previously described. In especially striking instances of these differences, therefore, they are claimed as new forms of matter.

In particular, the following substance is claimed as a new form of matter: diethoxydichlorotitanium, m.p. 80 to 84° C (m.p. 40 to 50° according to Encyclopedia of Chemical Technology, vol. 20, 2nd ed., p. 463), The substances prepared by the method of the invention find many uses in many different fields. For example, they serve as catalysts or co-catalysts for the polymerization and copolymerization of olefins, vinyl chloride, styrene, dienes, vinyl ethers, epoxides, alkylene oxides and aldehydes, as esterification and transesterification catalysts in organic and organometallic monomer chemistry, and in the preparation of saturated and unsaturated polyesters, polyester amides and imides, and polyamides by means of polycondensation and polyaddition reactions, in varnishes and resins as bonding agents, for thixotropication, for the modification of rheological properties, and as processing aids, for the surface treatment of glass and mineral substances, as improving agents for textiles, leather and paper, for example, especially for binding, repellentizing or dulling, for the production of special ceramic, as an adhesive component in cements, and in the production of glass fiber-reinforced plastics etc.

EXAMPLES

The following examples will explain the invention, without limiting its scope.

EXAMPLE 1a

The reaction apparatus consists of a heated 1,000-ml multinecked flask with internal thermometer, stirrer, dropping funnel and reflux condenser.

285 g=1.5 mol of $TiCl_4$ in 700 ml of n-hexane is placed in the flask. To it is added, drop by drop, at room temperature, with stirring, 156 g=1.5 mol of $(H_3C)_3Si(OCH_3)$. A yellow precipitate forms, and the internal temperature rises from 22° C. to 62° C. The mixture is stirred for about 45 minutes, while additional precipitate settles as the mixture cools. Then the precipitate is filtered off and vacuum dried. 264 g of $(CH_3O)TiCl_3$ is obtained as a light yellow powder.

EXAMPLE 1b

The reaction apparatus described in example 1a is modified by using a 500-ml multi-necked flask. 47.5 g=0.25 mol of $TiCl_4$ is dissolved in 150 ml of dichloromethane, and 52 g=0.5 mol of $(H_3C)_3Si(OCH_3)$ is added slowly, with stirring. During the very exothermic reaction a pale yellow precipitate settles out. Then dichloromethane and trimethyl chlorosilane are distilled out on the rotary evaporator at 0.5 mbar. The product is 44.4 g of $(H_3CO)_2TiCl_2$ as a fine, pale yellow powder. M.p.: decomposition at 165 to 170° C.

EXAMPLE 2a

In a reaction apparatus like that described in example 1, 285 g=1.5 mol of $TiCl_4$ is chilled to 10° C. Over a period of 10 minutes, 177 g=1.5 mol of $(H_3C)_3Si(OC_2H_5)$ is added, drop by drop. A yellow precipitate forms, and the temperature rises continuously to as much as 50° C. Upon cooling to room temperature, additional yellow precipitate settles out. Then the trimethylchlorosilane that has formed is distilled out in vacuo at about 35° C. bath temperature. 299 g of $(C_2H_5O)TiCl_3$ is the product, in the form of a yellow powder which smokes strongly in air. M.p.: 81° C.

EXAMPLE 2b

In a reaction apparatus as described in example 1, 285 g=1.5 mol of $TiCl_4$ is chilled to 3° C. Over a period of 5 minutes, 354 g=3 mol of $(H_3C)_3Si(OC_2H_5)$ is added drop by drop. A yellow precipitate forms, and the temperature rises to 51° C. While the mixture is cooling to 8° C, additional precipitate settles out. Then the trimethylchlorosilane that has formed is distilled out. The product is 313 g of $(C_2H_5O)_2TiCl_2$ in the form of a pale yellow powder which slowly decomposes in humid air. M.p.: 80 to 83° C.

Analysis: Cl: 34.0% (calc. 33.9). Ti: 22.8% (calc. 22.9).

Infrared: Measured in $CCl_4$, and $CCl_4$ compensation in the reference beam.

Characteristic absorptions in $cm^{-1}$: 2992, 2970, 2948, 2938, 1470, 1450, 1400, 1385, 1357, 1270, 1160, 1110, 1072, 1022, 940, 878, 623, 575, 540, 480, 460.

EXAMPLE 2c

The reaction apparatus consists of a heated 500 ml multinecked flask which is equipped with an internal thermometer, stirrer, dropping funnel and a packed column (depth of packing 50 cm, inside diameter 50 mm) with an automatic head and reflux condenser. 148 g=1 mol of dimethyldiethoxysilane is placed in the flask at room temperature. Under the surface of the silane, 95 g=0.5 mol of $TiCl_4$ is added drop by drop over a period of 22 minutes. The temperature rises to 78° C. and the initially forming yellow precipitate dissolves. The dimethylmonoethoxychlorosilane that forms is distilled off, and a yellow-brown, highly viscous residue is obtained, which slowly crystallizes. 101 g of coarsely crystalline $(C_2H_5O)_2TiCl_2$ can be isolated.

Analysis: Cl: 34.6% (calc. 33.9). Ti: 22.1% (calc. 22.9).

The product has the same infrared absorption lines as that of example 2b.

EXAMPLE 2d

Analogously to 2c 178 g=mol methyl triethoxy silane was used instead of dimethyl diethoxy silane. On adding the $TiCl_4$ the temperature rose to 70° C. The formed methyl diethoxy chlorosilane was distilled off in vacuo to give 103 g of $(C_2H_5O)_2TiCl_2$.

EXAMPLE 2e

The reaction apparatus consists of a 2000-ml multi-necked flask with internal thermometer, stirrer, dropping funnel and reflux condenser.

708 g=6 mol of $(H_3C)_3Si(OC_2H_5)$ is placed in the flask and chilled to 6° C. Over a period of 15 minutes 570 g=3 mol of $TiCl_4$ is added drop by drop. The temperature rises to 58° C., while the solution turned cloudy above about 46° C. After the mixture cooled, the solid matter that formed was filtered from the trimethylchlorosilane on a frit filter, washed with heptane and vacuum dried. The product is 576 g of $(C_2H_5O)_2TiCl_2$ in the form of a light yellow powder.

Analysis: Cl: 33.6% (calc. 33.9). Ti: 22.8% (calc. 22.9).

Infrared analysis as in example 2b.

EXAMPLE 2f

The reaction apparatus consists of a heated 500 ml multi-necked flask with internal thermometer, stirrer and dropping funnel, plus a packed column (depth of packing 130 cm, diameter 50 mm) with an automatic column head and reflux condenser.

At room temperature 236 g=2 mol of $(H_3C)_3Si(OC_2H_5)$ was placed in the flask and 95 g=0.5 mol of $TiCl_4$ was added drop by drop over a period of 7 minutes. The temperature rises from 22° C. to 65° C. and a yellowish, slightly cloudy solution forms, which is heated to ebullition. The trimethylchlorosilane that formed in the reaction is continuously distilled off. In the bottom remains 152 g of a slightly viscous, yellow solution. Then the trimethylethoxysilane that did not react was distilled off in a water-jet vacuum and 108 g is obtained of a pale yellow, highly viscous liquid of the composition: $(C_2H_5O)_{2.7}TiCl_{1.3}$.

EXAMPLE 2g

The preparation of $(C_2H_5O)_2TiCl_2$ is performed similarly to example 2b. 380 g=2 mol of $TiCl_4$ and 472 g=4 mol of $(H_3C)_3Si(OC_2H_5)$ are used. From this is obtained 413 g of $(C_2H_5O)_2TiCl_2$. 600 ml of n-heptane and 200 g of $C_2H_5OH$ (=9.7% excess) are added to 410 g of this half ester. $NH_3$ is fed into the white suspension that forms until the liquid phase gives an alkaline reaction. The dosing is performed such that the reaction temperature does not exceed 60° C.

During the reaction time of about 5 hours the liquid volume is increased with another 500 ml of n-heptane. Then the precipitated $NH_4Cl$ is filtered off and washed with 350 ml of n-heptane. From the clear, slightly yellowish filtrate first the n-heptane is distilled off at 50° C. and 100 mbar, and then the residue is fractionally distilled through a 30-cm Vigreux column at 117° C. to 118° C. head temperature and a pressure of 2 mbar. 358.1 g of $Ti(OC_2H_5)_4$ is obtained as a water-clear, colorless liquid.

EXAMPLE 3a

In a reaction apparatus used as in example 1b, 132 g=1 mol of $(H_3C)_3Si(O-n-C_3H_7)$ is heated at 65° C. To this 190 g=1 mol of $TiCl_4$ is added drop by drop within 3 minutes, with stirring and without external heating. At the point where it enters a lemon-yellow precipitate immediately forms, and the bottom temperature increases to 94° C. Then the mixture is refluxed for 2 hours. While it is cooling a lemon-yellow precipitate again settles out. The trimethylchlorosilane that formed during the reaction is distilled out in the water-jet vacuum at a heating bath temperature of 50° C. The product is 212 g of $(n-C_3H_7O)TiCl_3$, a yellow, very moisture-sensitive powder.

EXAMPLE 3b

In a reaction apparatus as described in example 1b, 132 g=1 mol of $(H_3C)_3Si(O-n-C_3H_7)$ is heated to ebullition. Over a period of 50 minutes 95 g=0.5 mol of $TiCl_4$ is added cautiously drop by drop, with stirring; after half of it is added the slightly cloudy solution is lemon-yellow, and by the end of the addition it is yellow-brown. During the reaction time the bottom temperature drops to 67° C. Then the trimethylchlorosilane that has formed is distilled off in a water-jet vacuum at a 40° C. heating bath temperature. The product is 116 g of $(n-C_3H_7O)_2TiCl_2$ as a viscous, brown liquid which crystallizes in a few days.

Analysis: Cl: 29.5% (calc. 29.93%). Ti: 20.0% (calc. 20.22%).

$^1$H-NMR ($CDCl_3$/TMS) O—$CH_3$, tr. 4.54 ppm, 2 H; $H_3C$—$CH_2$, sext. 1.89 ppm, 2 H; $H_2C$—$CH_3$, tr, 1.09 ppm, 3 H.

EXAMPLE 4a

In a reaction apparatus as described in example 1b, 66 g=0.5 mol of $(H_3C)_3Si(O-i-C_3H_7)$ is added, with stirring, over a period of 2 minutes to 95 g=0.5 mol of $TiCl_4$. A gold-brown solution forms, and the bottom temperature rises from 22.5° C. to a maximum of 75° C. Then the mixture is let cool in air, and a pale yellow precipitate settles out. The trimethylchlorosilane formed during the reaction is distilled off in a water-jet vacuum at 40° C. heating bath temperature. The product is 107 g of $(i-C_3H_7O)TiCl_3$ as a grayish-white powder very sensitive to hydrolysis.

EXAMPLE 4b

In an apparatus like that described in example 1a, 398g=3 mol of $(H_3C)_3Si(O-i-C_3H_7)$ is heated to 50° C. Over a period of 9 minutes, 285 g=1.5 mol of $TiCl_4$ is added. The bottom temperature rises to 71.5° C. The mixture is refluxed for 2 hours and then allowed to cool, while a precipitate begins to settle out. The trimethylchlorosilane that has formed is distilled off in vacuo and 351 g of (i-$C_3H_7O$)$_2$TiCl$_2$ is obtained in the form of a grayish-white solid.

Analysis: Cl: 30.1% (calc. 29.93%). Ti: 20.3% (calc. 20.22%).

$^1$H-NMR (CDCl$_3$/TMS) O—C$\underline{H}$, hept. 4.93 ppm, 1 H; HC-(C$\underline{H}_3$)$_2$, d, 1.48 ppm, 6 H.

EXAMPLE 4c

The process descibed in example 4b is modified by filtering off and vacuum-drying the precipitate obtained when the reaction mixture cools. The product is 181 g of (i-$C_3H_7O$)$_2$-TiCl$_2$ in the form of white crystals. M.p.: 53 to 57° C.

Analysis: Cl: 29.8% (calc. 29.93%). Ti: 20.8% (calc. 20.22%).

$^1$H-NMR as in example 4b.

The mother liquor is worked up as described in 4b.

EXAMPLE 5a 730 g=5 mol of ($H_3C$)$_3$Si(O-n-$C_4H_9$) is heated to 80° C. in a reaction apparatus as described in example 2d. 950 g=5 mol of TiCl$_4$ is added drop by drop, with stirring. The mixture is refluxed for about 1 hour. After it cools, the trimethylchlorosilane that forms during the reaction is distilled off in a water-jet vacuum at about 50° C. heating bath temperature. One obtains 1115 g (n-$C_4H_9O$)TiCl$_3$ as a pale orange light and moisture sensitive powder.

EXAMPLE 5b 148 g=1 mol of ($H_3C$)$_3$Si(O-n-$C_4H_9$) is heated to 100° C. in a reaction apparatus as described in example 1b. Over a period of 5 minutes, 95 g=0.5 mol of TiCl$_4$ is added drop by drop with stirring, while a deep orange solution forms. After 30 minutes of refluxing followed by cooling, the trimethylchlorosilane that formed during the reaction is distilled off in a water-jet vacuum at 50° C. heating bath temperature. The product is 132.5 g of (n-$C_4H_9O$) $_2$TiCl$_2$ as an orange-red liquid.

EXAMPLE 6a 47.5 g=0.25 mol of TiCl$_4$ in 100 ml of heptane is heated at 106° C. in a reaction apparatus as described in example 1b. Over a period of 20 minutes, 36.5 g=0.25 mol of ($H_3C$)$_3$Si-(O-i-$C_4H_9$) is added drop by drop with stirring. After the mixture cools, with the formation of an orange-colored precipitate, heptane and the trimethylchlorosilane that formed during the reaction are distilled out in vacuo. 56 g of (i-$C_4H_9O$)TiCl$_3$ is obtained as an orange-red solid.

EXAMPLE 6b 146 g=1 mol of ($H_3C$)$_3$Si(O-i-$C_4H_9$) is heated at 50° C. in a reaction apparatus as described in example 1b. Over a period of 15 minutes 95 g=0.5 mol of TiCl$_4$ is added drop by drop with stirring. Most of the trimethylchlorosilane that has formed is distilled out at standard pressure, and the rest in vacuo. The product is 130 g of (i-$C_4H_9O$)$_2$TiCl$_2$as an orange-red, highly viscous fluid at first, from which white crystals then form. M.p. 52 to 53° C.

Analysis: Cl: 27.0% (calc. 26.76%). Ti: 18.1% (calc. 17.1%)

$^1$H—NMR (CDCl$_3$/TMS) O—C$\underline{H}_2$, d, 4.42 ppm, 2 H; H$_2$—C—C$\underline{H}$, m, 2.18 ppm, 1 H; $\underline{H}$C—(CH$_3$)$_2$, d, 1.03 ppm, 6 H.

EXAMPLE 7a 41.5 g=0.25 mol of ($H_3C$)$_3$Si(OC$_6H_5$) in 200 ml of dichloromethane is placed in a reaction apparatus as described in example 1b. Then 47.5 g=0.25 mol of TiCl$_4$ is added drop by drop, with stirring. The previously colorless solution immediately turns dark red and then begins to boil. After 30 minutes of refluxing, dichloromethane and the trimethylchlorosilane that has formed is removed by distillation in vacuo. The product is 61.5 g of (C$_6H_5O$)TiCl$_3$ as a dark violet solid.

Instead of dichloromethane, other inert solvents can be used, such as perchloroethylene, n-hexane, cyclohexane, n-heptane and xylene. EXAMPLE 7b 95 g=0.5 mol of TiCl$_4$ in 200 ml of CH$_2$Cl$_2$ is placed in an apparatus as described in example 1b. 166 g=1 mol of ($H_3C$)$_3$Si(OC$_6H_5$) is added with stirring. The solution immediately turns dark red and then begins to boil. After 30 minutes of refluxing, dichloromethane and the trimethylchlorosilane that forms are removed by vacuum distillation. The product is 150 g of (C$_6H_5O$)$_2$TiCl$_2$ as a dark red solid.

EXAMPLE 4c

Analogously to 7b 47.5 g=0.25 mol TiCl$_4$ were reached with 124.5g=0.75 mol ($H_3C$)$_3$SiOC$_6H_5$ to give 86 g of (C$_6H_5O$)$_3$TiCl as a red solid.

Instead of dichloromethane, other inert solvents can be used, such as n-hexane, cyclohexane, n-heptane, perchloroethylene and xylene.

EXAMPLE 8

Analogously to 7b 47.5 g=0.25 mol TiCl$_4$ were reached with 180 g=1 mol o-cresol trimethylsilylester to give 114 g Tetra-o-cresyl titanate as a dark red solid.

It will be understood that the specification and examples are illustrative but not limitative of the present invention and that other embodiments within the spirit and scope of the invention will suggest themselves to those skilled in the art.

What is claimed is:

1. A method for the preparation of metallic acid esters of the formula (RO)$_n$MeX$_{4-n}$, in which Me is a metal selected from the group consisting of titanium, zirconium and hafnium, R represents an identical or different saturated or unsaturated aliphatic or aromatic hydrocarbon moiety, X is halogen, and n has a value from 1 to 4 comprising: selectively esterifying a corresponding metal halide with an amount of an organosilane ester of the formula R'$_n$Si(OR)$_{4-n}$ where R has the definition given above, R' represents identical or different alkyl groups of 1 to 4 carbon atoms, and n=1, 2 or 3 to provide a desired degree of partial esterification with the proviso that when a metallic acid ester is desired wherein n has values of 3 to 4, reacting a metallic acid partial ester wherein n=1 to 3 with an organic hydroxy compound in the presence of an amine.

2. The method of claim 1, wherein the esterification is in an organic solvent.

3. The method of claim 1 wherein equimolar amounts of the metal halide and the organosilane ester are brought to reaction to produce the metallic acid ester with n=1.

4. The method of claim 1, wherein the metal halide is reacted with the organosilane ester in a molar ratio of 1:2 to produce the metallic acid ester with n=2.

5. The method of claim 1, wherein the metal halide is reacted with such an amount of organosilane ester that 3 moles of organosilane ester are used per mole of metal halide to produce the metallic ester with n=3.

6. A method for the preparation of a metallic acid aryl ester of the formula Me(OR)$_4$ in which Me is a metal selected from the group consisting of titanium, zirconium and hafnium and in which R is an unsubstituted aryl moiety, or an aryl moiety substituted by halogen, alkyl or nitro groups, comprising: reacting a metal halide with such an amount of an organosilane aryl ester that at least 4 moles of organosilane aryl ester are used per mole of metal halide.

7. The method of claim 1, wherein n has a value of 1 to 3, for the preparation of metallic acid ortho esters of the formula Me(OR)$_4$.

8. The method of claim 7, wherein diethoxydichlorotitanium is used for the preparation of tetraethylorthotitanate.

9. The method of claim 7, wherein di-n-propoxydichlorotitanium is used for the preparation of tetrapropylorthotitanate.

10. The method of claim 7, wherein di-isopropyldichlorotitanium is used for the preparation of tetraisopropylorthotitanate.

11. The method of claim 7, wherein di-isobutoxydichlorotitanium is used for the preparation of tetraisobutoxyorthotitanate.

12. A pure metallic acid ester of the formula $$Cl_2Ti(OR)_2$$

wherein R is ethyl, said ester having a melting-point range from 80 to 83° C.

* * * * *